United States Patent [19]

Wachi et al.

[11] Patent Number: 4,873,384
[45] Date of Patent: Oct. 10, 1989

[54] METHOD FOR PRODUCING DICHLOROETHANE

[75] Inventors: Shun Wachi; Yuusaku Ariki, both of Takasago; Hiroshi Oshima, Kobe, all of Japan

[73] Assignee: Kanegafuchi Kagaku Kogyo Kabushiki Kaisha, Osaka, Japan

[21] Appl. No.: 338,538

[22] Filed: Apr. 14, 1989

Related U.S. Application Data

[63] Continuation of Ser. No. 105,496, Oct. 2, 1987, abandoned, which is a continuation of Ser. No. 830,801, Feb. 19, 1986, abandoned.

[30] Foreign Application Priority Data

Feb. 19, 1985 [JP] Japan .................................. 60-31261
Apr. 9, 1985 [JP] Japan .................................. 60-76277
May 22, 1985 [JP] Japan .................................. 60-111047

[51] Int. Cl.$^4$ .................... C07C 17/02; C07C 19/045; C07C 17/38
[52] U.S. Cl. .................................. 570/247; 570/246; 570/262
[58] Field of Search ............................... 570/246, 247

[56] References Cited

U.S. PATENT DOCUMENTS

| 2,929,852 | 3/1960 | Benedict | 570/246 |
| 3,597,465 | 8/1971 | Karafian et al. | 203/25 |
| 4,347,391 | 8/1982 | Campbell | 570/252 |
| 4,672,142 | 6/1987 | Hundeck et al. | 570/247 |

FOREIGN PATENT DOCUMENTS

| 53335 | 6/1982 | European Pat. Off. | 570/253 |
| 75742 | 4/1983 | European Pat. Off. | 570/247 |
| 760308 | 10/1956 | United Kingdom | 570/252 |
| 1056522 | 1/1967 | United Kingdom | 570/252 |
| 1184576 | 3/1970 | United Kingdom | 570/252 |

Primary Examiner—J. E. Evans
Attorney, Agent, or Firm—Armstrong, Nikaido, Marmelstein, Kubovcik & Murray

[57] ABSTRACT

A method for producing dichloroethane (EDC) by reacting ethylene and chlorine in a liquid reaction medium composed mainly of EDC at a temperature of not less than the boiling point of EDC measured at ordinary pressure, characterized by leading the vapor of the reaction medium generated in a reactor from the top of the reactor to a heat exchanger so as to recover and utilize the latent heat resulting from condensation of the vapor in the heat exchanger. According to the present invention, high heat utilization efficiency can be attained with advantages as compared with conventional EDC production methods.

4 Claims, 4 Drawing Sheets

METHOD FOR PRODUCING DICHLOROETHANE

This application is a continuation of application Ser. No. 105,496 filed Oct. 2, 1987, now abandoned, which in turn is a continuation of application Ser. No. 830,801 filed 2/19/86, now abandoned.

BACKGROUND OF THE INVENTION

The present invention relates to a method of producing dichloroethane (ethylene dichloride) (hereinafter referred to as "EDC") by reacting ethylene and chlorine in a liquid phase at a temperature not lower than 83° C. More particularly, the invention relates to a method of producing EDC wherein the heat of reaction is recovered for efficient utilization.

EDC is industrially important as a starting material in the production of vinyl chloride monomer. Since disclosure in U.S. Pat. No. 2,929,852, a method of reacting ethylene with chlorine at a temperature not lower than 83° C. by feeding the reactants into a liquid reaction medium composed mainly of EDC is known as the so-called high temperature method. The method is advantageous as compared with the low-temperature method in that the heat of reaction can be utilized more efficiently. In accordance with the method proposed in the above U.S. patent, a reaction-distillation scheme is adopted, namely the liquid reaction medium is vaporized by the heat of reaction and the vapor generated is introduced for purification into a distillation column connected with the upper part of the reactor, so that the heat of reaction can be efficiently utilized as a source of energy required for purification of EDC.

In British Patent No. 1,231,127, it is proposed that the heat of reaction should be efficiently utilized by purifying, according to the above reaction-distillation technique, not only EDC produced by the above reaction but also EDC obtained from the oxychlorination step in a vinyl chloride monomer production plant and the unreacted EDC obtained from the cracking step. In U.S. Pat. No. 4,172,099, an improvement is proposed which comprises supplying the EDC from the oxychlorination step to the above-mentioned reaction-distillation step after washing, neutralization, dehydration, low-boiling fraction elimination and like steps and, for the EDC from the cracking step, supplying it to the reaction-distillation step after passing through a step of chlorination. In Japanese patent Publication Kokai No. 90206/78, an improved method is proposed which comprises supplying the EDC recovered from the cracking step to the above reaction-distillation step after passing through a step of chlorination and then a step of removing high-boiling chlorinated components by distillation.

The heat of reaction in the production of EDC by reacting ethylene with chlorine is about 50 kcal/mol. This is about 7 times the quantity of heat required for vaporizing the EDC produced in this reaction. Therefore, when the reaction-distillation is conducted using this heat, a sufficient quantity of vapor can be produced for purifying the EDC from the oxychlorination step and the unreacted EDC from the cracking step as well as the EDC formed from ethylene and chlorine. However, as pointed out in Japanese Patent Publication Kokai No. 90206/78, if the unreacted EDC from the cracking step is fed to the reaction-distillation step, chloroprene and chlorinated derivatives thereof contained in the unreacted EDC exert an adverse influence on the reaction to decrease the selectivity of reaction and, as a result, the yield is markedly decreased. Feeding of the EDC from the oxychlorination step, which contains impurities such as water, ethylene chlorohydrin and chloral, to the reaction-distillation step is also unfavorable since such impurities cause significant corrosion of materials of construction and adversely influence the selectivity of reaction.

For the reasons mentioned above, only the EDC formed from ethylene and chlorine is applicable to the reaction-distillation technique for purification by distillation. For the removal of impurities in the unreacted EDC or the EDC from the oxychlorination step, some other energy source is required, as explained in Japanese Patent Publication Kokai No. 90206/78 or U.S. Pat. No. 4,172,099. Thus, in the prior art, the heat of reaction is not utilized efficiently and energy saving is insufficient.

Another drawback of the conventional reaction-distillation technique is that the content of low-boiling impurities in the purified EDC is high as compared with the case where low-boiling fraction removal and high-boiling fraction removal are conducted in order. In the process comprising taking out high-boiling impurities from the column bottom, low-boiling impurities from the column top and the purified EDC from the middle of the column, the content, in the purified EDC, of low-boiling impurities such as ethyl chloride is significant and these impurities exert an unfavorable influence on the cracking step for vinyl chloride monomer production.

A further drawback is that, in the reaction-distillation method, high-boiling impurities are concentrated in the reactor and cause a boiling point elevation, hence a rise in the reaction temperature, so that it is difficult to maintain the selectivity of reaction favorably. It is also a drawback that, in extracting high-boiling impurities from the column bottom, catalysts, such as ferric chloride, generally used and present in the reaction mixture flow out and make it difficult to maintain the catalyst concentration in the reaction mixture at an adequate level. Furthermore, it is necessary to treat the iron-containing discharge liquid.

As a method of efficient utilization of the heat of reaction which is other than the reaction-distillation method, Japanese Patent Publication Kokai No. 74624/83 proposes a liquid circulation technique which comprises leading the liquid reaction medium in the reactor to a heat exchanger so that the sensible heat possessed by the medium can be utilized efficiently. In sensible heat utilization, a larger quantity of liquid has to be circulated as compared with the case where the latent heat of condensation of a vapor is utilized, thus the power cost for liquid circulation is increased. In addition, the cost of equipment is increased because of necessity of a larger heat exchanger due to a smaller heat transfer coefficient as compared with the heat transfer upon condensation or, in using the liquid as the heat source for a distillation column reboiler, unfavorable operations are required, for instance, operation to increase the temperature difference in the heat exchanger by operating the distillation column under reduced pressure to thereby lower the distillation temperature.

For keeping a favorable selectivity of reaction in the above high-temperature process, it is effective to use ethylene in excess relative to chlorine, as proposed in British Patent No. 1,184,576. When ethylene is used in excess, unreacted ethylene is discharged. Therefore, for securing a high raw-material-based yield, it is important to recover the unreacted ethylene discharged. On the other hand, the chlorine used in this process is mostly produced on a commercial scale by electrolysis of sodium chloride. The chlorine produced by mercury process contains about 0.2 to 0.5% of oxygen, and the chlorine produced by diaphragm process contains about 1 to 2% or more of oxygen. As described in Japanese Patent Publication Kokai No. 177928/83, oxygen is effective for maintaining the selectivity of the reaction on a good level and, for producing this effect, the oxygen contained in the chlorine or an additional quantity of oxygen can be utilized. The oxygen thus supplied to the reactor goes with and is contained in the discharge gas together with the unreacted ethylene and, therefore, it is important to take into consideration the risk that the discharge gas might form an explosive mixture composition.

Among the known methods of recovering the unreacted ethylene, the method disclosed in British Patent No. 1,184,576 comprises cooling the reaction medium vapor generated by the heat of reaction in a high-temperature process, separating the resulting EDC by condensation and supplying the uncondensed gas to a second reactor to thereby attain recovery of the unreacted ethylene. For this method, it is described that an inert gas is added to the uncondensed gas, and accordingly formation of explosive mixture compositions can be avoided. However, when an inert gas such as nitrogen is added to the unreacted ethylene discharge, the concentration of ethylene to be supplied to the second reactor is lowered by dilution with the inert gas and, as a result, ethylene absorption becomes difficult.

As an alternative, Japanese Patent Publication Kokai No. 57906/73 (Societa Italiana) proposes a method comprising carrying out the reaction in two steps by supplying at most 88% of ethylene to a second reactor in the unreacted state. Since the ethylene content in the discharge is high, formation of an explosive mixture can be avoided. When the load onto the second reactor is great, however, the above method is disadvantageous in that the heat recovery for efficient utilization of the heat of reaction as generated by the high-temperature reaction in the first reactor is decreased.

It is one of the problems encountered by the high-temperature method that the selectivity and the yield of the desired EDC are decreased, because by-products, including 1,1,2-trichloroethane, are formed in increased amounts as compared with the low-temperature method.

As methods proposed for inhibiting a side reaction which gives 1,1,2-trichloroethane in the high-temperature process, there are mentioned, for instance, a two-step reaction method disclosed in Japanese Patent Publication Kokai No. 57906/73 wherein the high-temperature reaction conducted using a large excess of ethylene and the low-temperature reaction for converting the excess ethylene are combined, a method of inhibiting side reactions chemically using an additive, such as a cresol (Japanese Patent Publication Kokai No. 40620/81), benzene or the like (Japanese Patent Publication Kokai No. 50203/83), or an amine (Japanese Patent Publication Kokai No. 104636/83).

A primary object of the present invention is to provide a method for producing EDC which is higher in heat utilization efficiency than the conventional reaction-distillation method and has no problems in selectivity of reaction and quality of product as encountered by the reaction-distillation technique and which is more efficient in recovery and utilization of reaction heat than the liquid circulation method.

The above and other objects of the present invention will become apparent from the description hereinafter.

SUMMARY OF THE INVENTION

It has now been found that the heat of reaction can be recovered and utilized more efficiently than conventional methods by recovering the latent heat of the reaction medium vapor using a heat exchanger.

In accordance with the present invention, there is provided a method of producing dichloroethane which comprises feeding ethylene and chlorine into a liquid reaction medium containing dichloroethane as a main component in a reactor, reacting the ethylene and chlorine at a temperature which is not lower than the boiling point of dichloroethane at ordinary pressure, to produce dichloroethane, leading the vapor of the reaction medium generated in the reactor from the top of the reactor to a heat exchanger, and recovering the latent heat resulting from condensation of the vapor in the heat exchanger.

DETAILED DESCRIPTION

The reactor to be used in the practice of the invention may be of the tower type, of the vessel type or further of the loop- or double pipe-shaped liquid circulation type. The reactor is charged with a liquid reaction medium in which EDC (dichloroethane) is the main component, and thereto are fed ethylene and chlorine and the reaction is allowed to proceed at a temperature not lower than 83° C. to produce EDC. The ethylene and chlorine are preferably fed in amounts such that ethylene is stoichiometrically in excess. Thus, the ethylene/chlorine ratio can be from 1.001 to 1.200. Iron chloride or known other catalytically active substances may be used as catalysts for the reaction. Oxygen is also preferred for improving the selectivity of reaction. Oxygen is supplied to the reactor generally in admixture with chlorine, the oxygen content in chlorine in that case being usually from 0.1% to 10% by mole. Also, known side reaction inhibitors such as benzene or derivatives thereof, cresol or derivatives thereof and amine compounds, or a chlorinated aliphatic unsaturated hydrocarbon of the formula:

wherein n is an integer of 1 to 3, may be included in the liquid reaction medium. The chlorinated aliphatic unsaturated hydrocarbon is, for example, tetrachloroethylene (when n=1) or hexachloro-1,3-butadiene (when n=2), and is caused to exist in the reaction medium in an amount of not less than 0.001% by weight, preferably within the range of 0.005 to 0.1% by weight. When the amount is less than 0.001% by weight, the side reaction inhibiting effect cannot be produced. On the other hand, at concentrations above 0.05% by weight, the effect remains nearly constant in spite of further increase in concentration and, therefore, the use in an amount of at most about 0.1% by weight is practical.

Tetrachloroethylene or hexachloro-1,3-butadiene can be assayed by gas chromatography or other means. Therefore, such an additive can be maintained at a preferable concentration by analyzing its concentration in the reaction medium at need and, if deficient, supplementing it. In the case where such a additive is discharged from the system together with the produced EDC, or in similar cases, the additive may be added continuously to the reactor. In cases where such a chlorinated aliphatic unsaturated hydrocarbon is formed as a reaction product in a small amount, the intended object can be attained by concentrating this product to a desired concentration. It is also possible to use both the concentration and addition operations.

The heat generated by the reaction of ethylene and chlorine is partly or wholly consumed for the vaporization of the liquid reaction medium and, as a result, the reactor temperature is maintained at a constant level.

The most characteristic feature of the present invention resides in that the reaction medium vapor is introduced into a heat exchanger connected with the upper part of the reactor and condensed there for recovery of the latent heat, thereby efficiently utilizing the reaction heat. Since a higher condensation temperature in the heat exchanger enables efficient utilization of the heat recovered, the reaction temperature is set at 83° C. or above, more preferably at 100° to 160° C.

In the distillation for purifying EDC, the operation for removing high-boiling impurities requires a particularly large quantity of heat energy. Therefore, the heat recovered in the heat exchanger is most preferably used as a heat source for a reboiler of a distillation column used for removing high boiling impurities (this distillation column being hereinafter referred to as "high-boiling column"). This is effective in simultaneously distilling together the unreacted EDC from the cracking step and/or the EDC from the oxychlorination step, because it is not required to pass through steps of chlorination, etc.

In case where the quantity of heat required for the reboiler of the high-boiling column is excessively larger than the heat of reaction or in case where the distillation column operation temperature is too high as compared with the reaction temperature, it is possible to provide a side reboiler, thereby applying the recovered heat to the middle of the high-boiling distillation column, while supplying some other energy to the distillation column bottom.

Alternatively, taking into consideration the energy utilization in the whole vinyl chloride monomer plant, it is also possible to utilize the heat recovered by the heat exchanger as a heat source for preheating or evaporating the liquid EDC, a heat source for elevating temperature or evaporating liquefied ethylene or hydrogen chloride, or a heat source for a distillation column for EDC, hydrogen chloride or vinyl chloride monomer.

In this manner, diversified approaches can be made for efficient energy utilization.

The heat exchanger to be used may be a shell-and-tube heat exchanger of the thermosiphon type, kettle type or falling film type, and other heat exchangers. A preferable type is selected from the viewpoints of the heat transfer coefficient of heat-receiving side, scale adhesion, site area, cleaning method and so on.

It is possible to provide a gas-liquid contact device in the upper part of the reaction column, in other words, between the top of the reactor and the heat exchanger so that droplets of the reaction mixture are prevented from flowing out of the reactor by bringing the reaction medium vapor into contact with the condensate liquid formed in the heat exchanger, whereby the catalyst in the reaction mixture is also prevented from flowing out. Furthermore, such device can also serve to concentrate the chlorinated aliphatic hydrocarbon used for preventing a side reaction, thereby maintaining it in the liquid reaction medium. Usual multiplate columns or packed columns may be used as the gas-liquid contact device. In case of not using such a gas-liquid contact column, an increased amount of the side reaction inhibitor is discharged together with the reaction medium. It is not preferable to distill and purify EDC in the gas-liquid contact column connected with the top of the reactor, since the side reaction inhibitor is also discharged when a high-boiling impurity concentrate liquid is drawn out of the column at a site near the bottom.

It has been found that hexachloro-1,3-butadiene, which is one of the side reaction inhibitors usable in the invention, is formed in a trace amount in the reactor. Therefore, when hexachloro-1,3-butadiene is concentrated in the reaction mixture by connecting a gas-liquid contact column to the top of the reactor in accordance with a preferred embodiment of the invention, the hexachloro-1,3-butadiene concentration can be maintained at a preferred level without particular addition of a side reaction inhibitor.

In the above case, the condensate liquid formed in the heat exchanger is mostly returned to the reactor, while a part thereof is taken out of the reactor as a product EDC. The product EDC thus drawn out is supplied to a distillation column where low-boiling impurities in the EDC are separated by simple distillation and drawn out from the distillation column top. The impurity fraction can be introduced into the gas-liquid contact section of the reactor column. Even if steam or the like is used as the heat energy for the above simple distillation, the steam drawn out from the column top can be introduced into the upper part of the reactor and arrives at the heat exchanger with the reaction medium vapor, whereby the heat of steam can be recovered.

After removal of low-boiling impurities by simple distillation, the product EDC drawn out from the reactor can be sent together with the EDC produced by oxychlorination process and/or the unreacted EDC from the thermal cracking step, to the high-boiling column wherein the heat of reaction is utilized, for further purification of the EDC. In this way, the heat of reaction can be recovered and utilized for removing low-boiling and high-boiling impurities, whereby highly pure EDC can be obtained.

Since the reaction medium vapor generated from the reactor contains, in addition to low-boiling impurities, also unreacted ethylene, oxygen and so on, uncondensed components may remain if the condensation temperature in the heat exchanger is high. Such uncondensed components may be further subjected to deep cooling so that useful components can be recovered. It is preferable, however, to take out the uncondensed components together with the EDC vapor and introduce the mixture into a second reactor in which the unreacted ethylene is recovered. If accompanied by a sufficient quantity of the EDC vapor, the ethylene and oxygen in the uncondensed components can be prevented from constituting an explosive mixture composition, thus the process can be operated safely.

Figure 2:
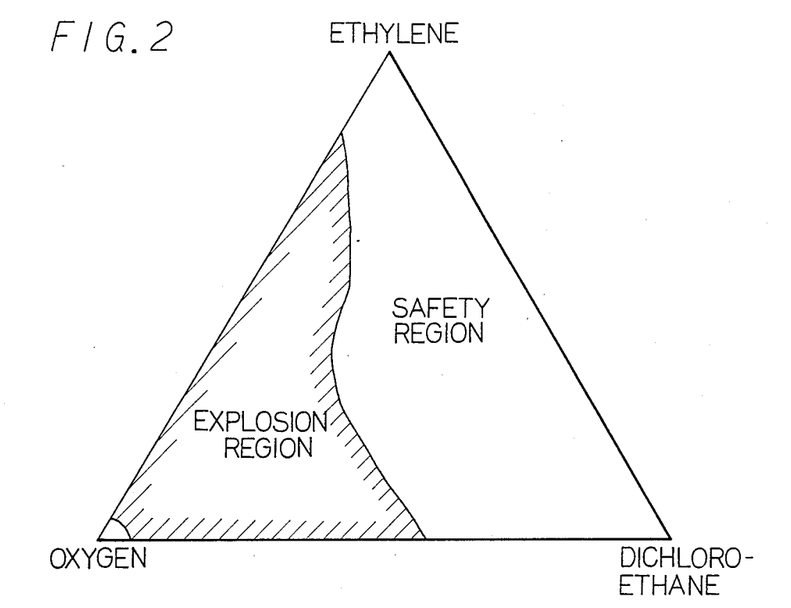
FIG. 2 is a triangular diagram illustrating the explosion region of a ternary mixture of ethylene, oxygen and EDC.
Figure 3:
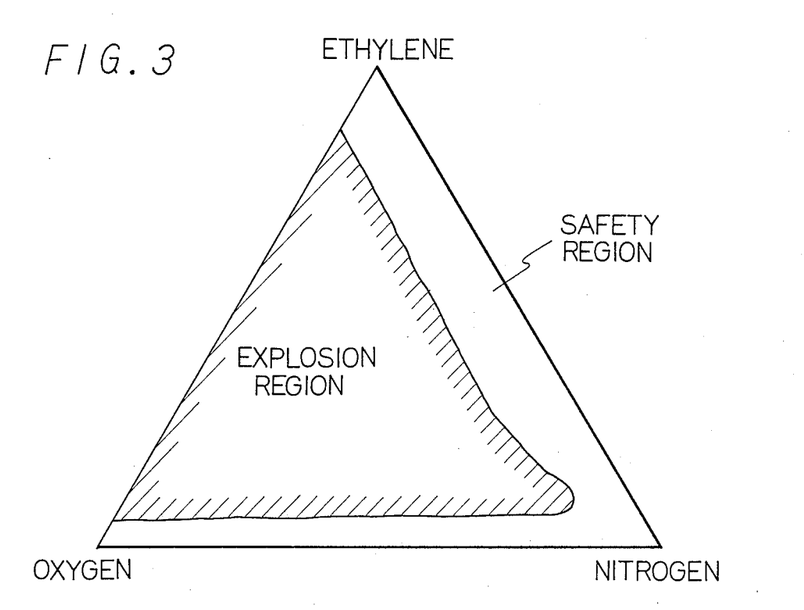
FIG. 3 is a triangular diagram illustrating the explosion region of a ternary mixture of ethylene, oxygen and nitrogen.

The region of explosive mixture composition for the case in which an incombustible gas, such as nitrogen, is used for dilution is shown in FIG. 3. On the contrary, when the EDC obtained in the form of the reaction medium vapor is used as a third component for avoiding formation of an explosive mixture, the safety region is wide, as shown in FIG. 2. This is a further advantageous feature of the invention.

The quantity of the vapor to be kept uncondensed in the heat exchanger can be selected within the range of 0.05 to 1.0 mole per mole of the chlorine fed to the first reactor. In ordinary reactor operation, the quantity of excess ethylene and/or the oxygen content are determined in most cases based on the number of moles of the feed chlorine. Therefore, it is convenient for process control for avoiding formation of an explosive mixture to determine the quantity of the uncondensed vapor on the same basis, since the proportions of the oxygen, ethylene and EDC in the discharge gas can be determined. If the quantity of uncondensed vapor is too small, there is a risk that an explosive mixture composition might be constituted and, if the quantity is excessive, the quantity of the condensate to be returned to the first reactor becomes insufficient, which makes it difficult to maintain the quantity of the liquid in the reactor, or the quantity of heat recovered in the condenser (heat exchanger) becomes small. To avoid these and other disadvantages, it is preferable to select an appropriate quantity of uncondensed vapor. It is in particular preferable to select the above quantity within the range such that the proportion of EDC in the uncondensed gas discharge is maintained at 30% by volume or more. This range falls within the safety region as shown in FIG. 2 which illustrates the explosive mixture composition. It is also possible to operate within the safety region by maintaining the oxygen concentration low.

In order to confirm that the discharge gas has not an explosive mixture composition but is safe, it is preferable, for example, to measure the rate of flow of the discharge gas or to analyze the composition of the discharge gas. Based on the results of such a detection, a more appropriate quantity of the uncondensed gas can be selected.

If oxygen is concentrated in the uncondensed gas, there is a risk of formation of an explosive mixture composition. On the contrary, dilution to a sufficient quantity of vapor in accordance with the invention keeps the oxygen concentration at low levels, so any explosive mixture composition cannot result at all.

The adjustment of the uncondensed vapor quantity required in the practice of the invention can be attained, for instance, by controlling the condensation temperature or pressure. Thus, by knowing the relationship between the temperature and vapor pressure of EDC which is the main component of the reaction medium, it becomes possible to maintain in the uncondensed state the vapor of the quantity which corresponds to the partial pressure of EDC vapor at the condensation temperature under a given pressure.

The unreacted ethylene discharged from the reactor (first reactor) together with the reaction medium vapor as adjusted in the above manner is supplied to the second reactor. By using as the second reactor an absorption column in which a liquid reaction medium containing EDC as the main component is maintained at a lower temperature as compared with the first reactor, the reaction medium vapor obtained from the first reactor is condensed rapidly, and accordingly the unreacted ethylene is absorbed rapidly and thus recovered. As the second reactor, a liquid-phase chlorination reactor used for the low-temperature process in a vinyl chloride monomer production plant may be used, or an oxychlorination reactor be used as well.

If the quantity of the unreacted ethylene discharged from the first reactor is too large, the recovery and utilization of heat becomes less advantageous, namely the condensation temperature lowers or the heat transfer coefficient lowers in latent heat recovery from the reaction medium vapor in the heat exchanger. Whereas the quantity of the feed ethylene should preferably be excessive with respect to chlorine so that the quantity of the unreacted chlorine discharged can be suppressed to a low level, the quantity of the unreacted ethylene discharged from the reactor should preferably be maintained at 5.0% or lower based on the quantity of ethylene fed to the reactor. The use as the reactor of a liquid circulation type one, such as a loop type or double pipe type one, is preferable because good mixing can be attained by the stirring effect produced by the circulating current, but results in increase of unreacted ethylene as a result of decrease in gas absorption efficiency. In case of using a liquid circulation reactor, the quantity of unreacted ethylene can be reduced by constructing only the lower part of the reactor to a circulation type, thereby preventing ethylene from passing through the reactor without reacting with chlorine.

According to the process of the present invention, advantages as mentioned below can be obtained. A high heat utilization efficiency can be attained by recovering and utilizing the heat of reaction in accordance with the present invention, thereby saving the heat energy, such as steam, required in the prior art by a quantity of heat approximately corresponding to the heat of reaction. The heat utilization is not so limited and can be utilized for various purposes. Even in case of using as a heat source for distillation of EDC, an existing distillation column can be used as it is and the quality of the product EDC is not affected adversely, since the heat is utilized indirectly through the heat exchanger. Also, the heat transfer efficiency in heat exchange is good, since the latent heat of condensation of the reaction medium vapor is recovered.

In accordance with the invention, the liquid in the reactor need not be drawn out and, therefore, it is not necessary to adjust the catalyst concentration by adding the catalyst from the outside or to treat an iron-containing high-boiling fraction. Since the condensation temperature in the heat exchanger is high and therefore the unreacted ethylene and oxygen in the uncondensed gas are in a state diluted with the EDC vapor, the invention produces the effect of allowing safe operation while avoiding explosive mixture compositions. In particular, when the uncondensed gas is introduced into the second reactor for the production of EDC from the unreacted ethylene, the method according to the invention is advantageous in that particularly pressurized nitrogen as needed in the prior art is no more necessary. The safety region forming no explosive mixture composition in the case where EDC is used as a third component to be added to oxygen and ethylene is wide as compared with the case where nitrogen is used as the third component in accordance with the prior art. Therefore, the allowable range of load variation in the reactor or variation in the operational condition becomes wide and this is advantageous from the operational procedure viewpoint. A further advantage is that since the quantity of gas required for dilution to attain a composition within the safety region is smaller in the case where EDC is used as the diluent gas as compared with the case where nitrogen is used, the scale of equipment can be reduced. When the unreacted ethylene in the discharge gas to be fed to the second reactor is diluted with nitrogen in accordance with the prior art, the ethylene concentration is low and therefore the ethylene is absorbed into the solvent slowly and can hardly be recovered. On the contrary, in accordance with the method of the invention, EDC is condensed rapidly in the second reactor which is maintained at a lower temperature, and accordingly the unreacted ethylene is concentrated significantly and absorbed rapidly, hence can be recovered with ease.

When a large excess of ethylene is fed in accordance with the prior art, the proportion of ethylene which undergoes the high-temperature reaction in the first reactor is small, so the heat utilization efficiency is low even if utilization of the heat of high-temperature reaction is desired. On the contrary, the method according to the invention is advantageous in that since it is not necessary to increase the unreacted ethylene content to an excessive level, the rate of heat recovery and utilization can be increased, and also from the equipment cost standpoint, it is advantageous in that the load on the second reactor is light.

When a chlorinated aliphatic unsaturated hydrocarbon, such as hexachloro-1,3-butadiene or tetrachloroethylene, is used as a side reaction inhibitor in accordance with a particularly preferred embodiment of the invention, by-product can be used as it is as an inhibitor with advantage. By reacting ethylene and chlorine in a liquid reaction medium containing EDC as the main component in the presence of the side reaction inhibitor, the amounts of side reaction products, such as 1,1,2-trichloroethane, can be reduced to a significant extent, and even in the high-temperature reaction, EDC can be produced in high yields. In this manner, the invention produces a further, but not less, effect of enabling commercial practice of the high-temperature process which has many advantages with respect to efficient utilization of the heat of reaction, EDC purification, etc.

The present invention is more specifically described and explained by means of the following Examples. It is to be understood that the present invention is not limited to the Examples, and various changes and modifications may be made in the invention without departing from the spirit and scope thereof.

EXAMPLE 1

Figure 1:
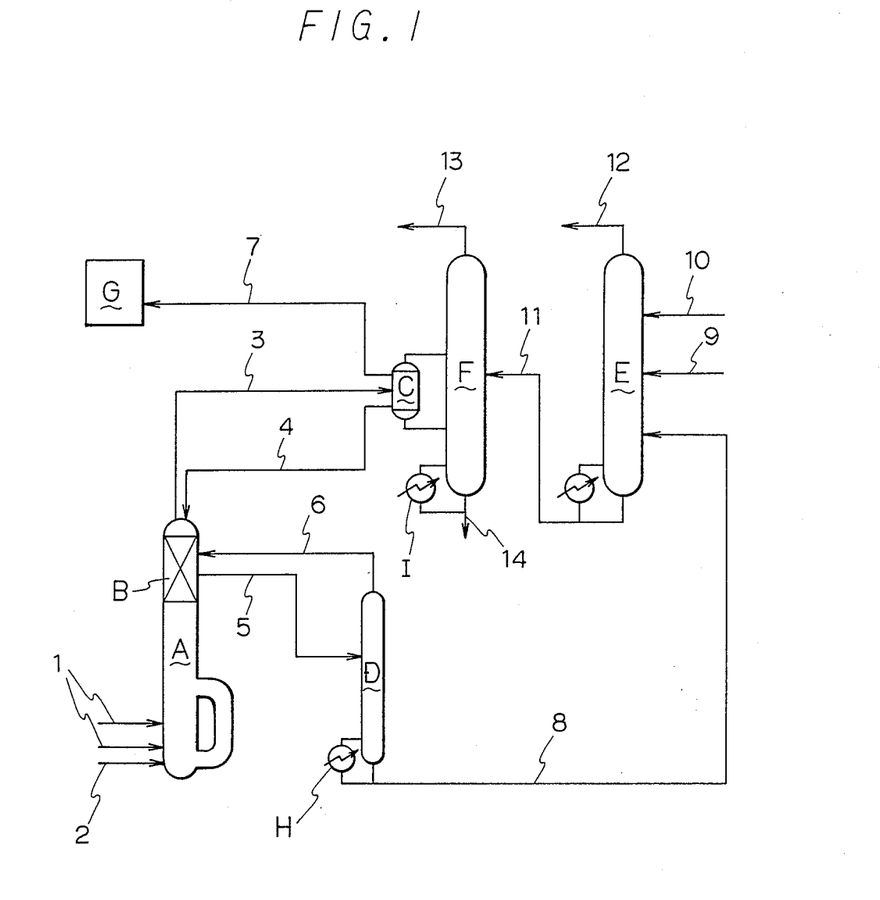
FIG. 1 is a flow diagram showing an embodiment of an EDC manufacturing apparatus used for practicing the process of the present invention.

EDC was prepared according to an embodiment of the present invention by using the apparatus shown in FIG. 1.

Reactor column A having an effective height of 6 m and equipped with a 3-meter circulation loop at the lower portion thereof was charged with liquid dichloroethane (EDC) and further with ferric chloride at a dissolved concentration of about 0.1% by weight. Ethylene was fed at a flow rate of about 2.04 ton/hr from near the bottom of the column through conduit 2, and chlorine containing about 2.0% by volume of oxygen which was divided into 2 portions, was fed at a flow rate of about 5.02 ton/hr to the lower part of the column through two conduits 1 provided at different heights. The reaction was conducted at 135° C. The reaction medium gone to boil due to the heat of reaction, thereby generating about 50 ton/hr of vapor. This vapor was fed to heat exchanger C through gas-liquid contact zone B via a conduit 3. The heat exchanger C was a side reboiler of a distillation column (high-boiling column) F for purification by removal of high-boiling fractions from EDC. Most of the reaction medium vapor was condensed to liquefy at about 125° C. and returned to the gas-liquid contact zone B via a conduit 4. The main components of the uncondensed gas discharged from the heat exchanger C into a conduit 7 were about 32 Nm$^3$/hr of oxygen, about 48 Nm$^3$/hr of ethylene, about 240 Nm$^3$/hr of EDC vapor, and other low-boiling impurities, and this gas was fed to second reactor G. The second reactor was a liquid-phase reactor operated at about 60° C. in which EDC containing about 200 wt. ppm of dissolved ferric chloride was charged. In the second reactor, the EDC vapor introduced through the conduit 7 was quickly condensed to liquefy, while ethylene was reacted with separately supplied chlorine.

The product EDC was withdrawn from the middle part of the gas-liquid contact zone B at a rate of about 6.5 ton/hr and fed to distillation column D through conduit 5. In the column D, the product EDC was distilled under the heat of steam supplied at a rate of about 0.1 ton/hr from reboiler H, and the vapor (low boiling components) from the column top was fed again to the gas-liquid contact zone B through conduit 6. The EDC obtained via the conduit 8 was fed to distillation column E in which low-boiling impurities were further removed through conduit 12. To the distillation column E, EDC obtained from the oxychlorination step and EDC recovered from the cracking step were also fed simultaneously for purification through conduits 9 and 10. The EDC withdrawn from the bottom of distillation column E was fed through conduit 11 to the distillation column F where high-boiling impurities were removed through conduit 14 and the purified EDC was obtained from the column top through conduit 13. The distillation column F had heretofore been operated by supplying steam to reboiler I to give the energy necessary for purification, but by utilizing the heat exchanger C as a side reboiler for recovery and re-utilization of the heat of reaction according to the present invention, there could be realized saving of about 7.0 ton/hr of steam in the purification of the conventional order.

EXAMPLE 2

Figure 4:
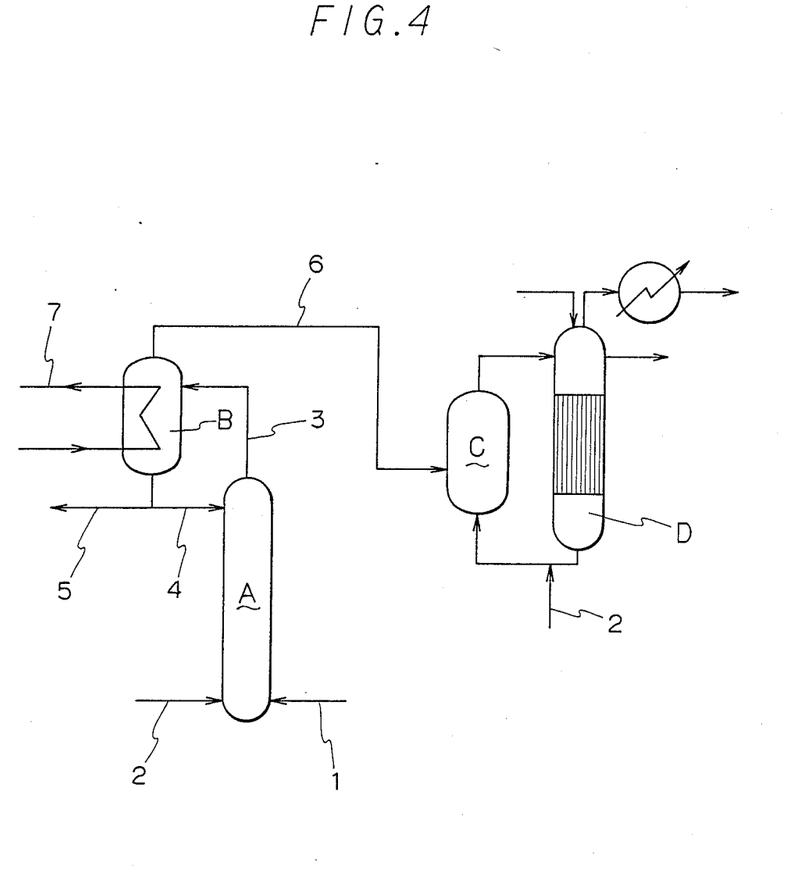
FIGS. 4, 5 and 6 are flow diagrams showing other embodiments of EDC manufacturing apparatuses used for practicing the process of the present invention.

EDC was produced by using the apparatus shown in FIG. 4. First reactor A was charged with EDC liquid and about 1,500 wt. ppm of ferric chloride was dissolved therein as a catalyst. Chlorine was fed from conduit line 2 at a rate of 700 kg/hr, while ethylene was fed from conduit line 1 at a rate of 287 kg/hr, and the reaction was conducted at about 2% by mole excess of ethylene. The chlorine contained 2% by mole of oxygen. With the reactor column top pressure maintained at 4 atm, the liquid reaction medium was boiled at 135° C. to maintain the temperature constant. The vapor of the reaction medium gasified by the heat of reaction was fed to heat exchanger B through the conduit line 3. The condensation temperature in the heat exchanger B was controlled at 124° C. by adjusting heat medium 7. A portion of the condensate was withdrawn as a product through conduit 5, while the remainder was returned to the reactor A through conduit 4. The vapor pressure of EDC at 124° C. was about 3.08 atm, which was about 75% of the total pressure. The components withdrawn as uncondensed gases from conduit 6 to feed to second reactor C were about 4,400 Nl/hr of oxygen, about 4,400 Nl/hr of ethylene, about 33,200 Nl/hr of EDC and about 2,000 Nl/hr of other components. Since this composition was within the safety region indicated in FIG. 2, it was not explosive. The total amount of gas flowing through the conduit 6 was measured and the condensation temperature was adjusted to ensure an appropriate flow rate. The second reactor C charged with EDC and connected to an external heat exchanger D was maintained at 60° C. The fraction from the conduit 6 was fed to the reactor C and reacted with chlorine from conduit line 2, the amount of chlorine fed corresponding to the amount of unreacted ethylene. In this stage, the load on the first reactor was about 98% of the total load, and the heat of reaction in the first reactor was recovered by the heat medium 7 of the heat exchanger B for re-use. The load on the second reactor was about 2% of the total load, and the ethylene concentration after liquefaction of EDC was about 45%, thus recovery by absorption was quite easy. The total volume of discharge gas was about 44,000 Nl/hr. The heat of reaction was efficiently recovered to the amount of 98%.

EXAMPLE 3

The reaction was conducted in the same manner as in Example 2 except that ethylene was fed at 290 kg/hr, the ethylene excess being about 3%, and the oxygen content in chlorine was 2%. When the reaction temperature and the condensation temperature were maintained at 135° C. and 100° C., respectively, the components discharged as uncondensed gases from the conduit 6 were about 4,400 Nl/hr of oxygen, about 17,600 Nl/hr of ethylene, about 16,200 Nl/hr of EDC, and about 2,000 Nl/hr of others. This composition was within the safety region shown in FIG. 2.

The volume of discharge gas under the above conditions was about 40,000 Nl/hr. Compared with the first reactor, the ethylene loading for the second reactor C was as low as about 8% and the ethylene concentration after liquefaction of EDC was as high as about 75%. Therefore, recovery by absorption was easy. The heat of reaction was efficiently recovered to the amount of 92%.

EXAMPLE 4

The reaction was conducted in the same manner as in Example 2 except that chlorine was fed at 200 kg/hr, the oxygen content in the chlorine was 3%, and ethylene was fed at a rate of 80 kg/hr with an excess of about 1%. When the reaction temperature and the condensation temperature were maintained at 110° C. and 97° C., respectively, the EDC vapor pressure at this condensation temperature was 1.50 atm against the total pressure of 2.16 atm. The components discharged as uncondensed gases from the conduit 6 were about 1,900 Nl/hr of oxygen, about 630 Nl/hr of ethylene, about 6,100 Nl/hr of EDC, and about 100 Nl/hr of other gases. Thus, this composition was within the safety region shown in FIG. 2.

In this operation, the volume of the discharge gas was about 8,700 Nl/hr. The ethylene load on the first reactor was about 99% and the heat of reaction could be recovered. The load on the second reactor was as small as about 1% and the ethylene concentration after liquefaction of EDC was about 25%, thus recovery by absorption was easy.

EXAMPLE 5

The reaction was conducted in the same manner as in Example 2 except that chlorine was fed at a flow rate of 500 kg/hr, the oxygen content in the chlorine was 1.5%, and ethylene was supplied at a flow rate of 207 kg/hr with an excess of about 5% based on the chlorine. When the reaction temperature and the condensation temperature were maintained at 130° C. and 120° C., respectively, and the EDC vapor pressure at the condensation temperature was 2.7 atm against the total pressure of 3.7 atm, the components discharged as uncondensed gases were about 2,300 Nl/hr of oxygen, about 7,800 Nl/hr of ethylene, about 36,000 Nl/hr of EDC and about 1,500 Nl/hr of other gases. This composition was within the safety region shown in FIG. 2. The total volume of discharge gases was about 47,000 Nl/hr. The ethylene load on the second reactor was about 5% of the total load and the ethylene concentration after liquefaction of EDC was about 70%, thus permitting easy recovery by absorption. The heat of reaction was efficiently recovered to the amount of 95%.

EXAMPLE 6

The reaction was conducted in the same manner as in Example 2 except that chlorine was fed at a rate of 800 kg/hr, the oxygen content in the chlorine was 2.0%, and ethylene was fed at a rate of 121 kg/hr. The excess percentage of ethylene was about 2%. When the reaction temperature and the condensation temperature were maintained at 120° C. and 95° C., respectively, and the EDC vapor pressure at the condensation temperature was 1.42 atm against the total pressure of 2.80 atm, the components discharged as uncondensed gases were about 1,900 Nl/hr of oxygen, about 1,900 Nl/hr of ethylene, about 4,200 Nl/hr of EDC and about 300 Nl/hr of other gases. This composition was within the safety region shown in FIG. 2. The total volume of discharge gas under the above conditions was about 8,300 Nl/hr. The load on the second reactor was as small as about 2% of the total ethylene load and the ethylene concentration after liquefaction of EDC was about 50%, thus permitting easy recovery by absorption. The heat of reaction was efficiently recovered to the amount of 98%.

COMPARATIVE EXAMPLE 1

The reaction was conducted in the same manner as in Example 2 except that the condensation temperature was set at 50° C. The EDC vapor pressure at 50° C. was 0.308 atm relative to the total pressure of 4.018 atm. To avoid the explosive composition, ethylene feed was set at 325 kg/hr, which represented an excess of about 35%. The components discharged as uncondensated gases were about 4,400 Nl/hr of oxygen, about 76,600 Nl/hr of ethylene, about 6,800 Nl/hr of EDC and about 200 Nl/hr of other gases. Thus, the discharge gas formed a composition within the safety region with a large excess of ethylene, as shown in FIG. 2, and accordingly such a composition was safe irrespective of dilution with EDC. The volume of discharge gas was about 88,000 Nl/hr, which was greater than in Example 2. Since the load on the second reactor was as high as 26% of the total ethylene load, the equipment size had to be increased as compared with the one Example 2. Moreover, the recovery of heat produced by the high-temperature reaction in the first reactor was 74% of the total heat of reaction and this percentage was lower than the percentage that could be realized in accordance with Example 2.

COMPARATIVE EXAMPLE 2

The reaction was conducted in the same manner as in Example 2 except that the condensation temperature was set at 50° C. The EDC vapor pressure at this condensation temperature was 0.308 atm against the total pressure of 4.018 atm. To avoid the explosive composition, nitrogen gas was fed at a rate of about 72,200 Nl/hr. Under the above conditions, the components discharged as uncondensed gases were about 4,400 Nl/hr of oxygen, about 4,400 Nl/hr of ethylene, about 6,800 Nl/hr of EDC, about 72,000 Nl/hr of nitrogen and about 200 Nl/hr of other gases. This was within the safety region shown in FIG. 3, owing to dilation by nitrogen gas.

In the above operation, nitrogen pressurized to at least 4.018 atm had to be fed. Moreover, the volume of discharge gas was about 88,000 which was about twice as large as the volume in Example 2. The load on the second reactor was about 2% of the total ethylene load, which was the same as in Example 2, but since the ethylene concentration was as low as about 5%, absorption was much delayed as compared with Example 2 and thus, recovery was difficult.

EXAMPLE 7

Figures 5, 6:
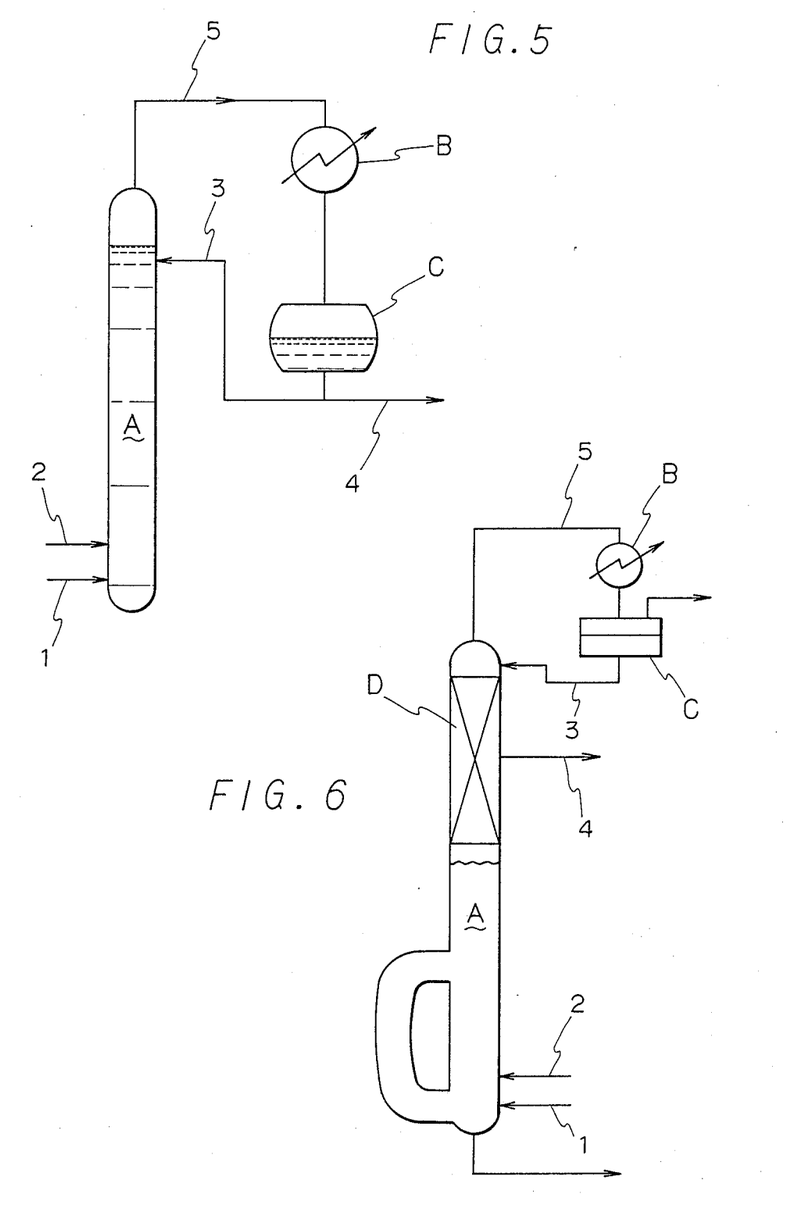

A stainless steel reactor A having a column diameter of 20 cm, shown in FIG. 5, was charged with liquid EDC to the level of 6 m and anhydrous ferric chloride was added thereto so that the concentration of dissolved ferric chloride was about 5 wt. ppm, followed by addition of hexachloro-1,3-butatiene at the level of 200 wt. ppm as dissolved. From near the bottom of the reactor, ethylene 1 and chlorine 2 were respectively fed at a flow rate of 40 Nm$^3$/hr. The chlorine contained about 1.5 mole % of oxygen. When the reactor top pressure was maintained at about 2.9 kg/cm$^2$G, the reaction temperature became about 135° C. Thus, the operation was feasible under boiling of the reaction medium. The EDC vapor gasified by the heat of reaction was withdrawn from the top, and fed to through conduit 5 and condensed in heat exchanger B. The condensate was guided into receptor C and a portion thereof was recycled through conduit 3 so as to maintain the liquid level in the reactor A, while the remainder was withdrawn as a product EDC through conduit 4. The heat of reaction could be recovered from the heat exchanger B. After about 50 hours of reaction, when the steady state had been established, the product EDC was sampled and analyzed by gas chromatography. The by-products were as shown below.

| | |
|---|---|
| 1,1,2-Trichloroethane | 0.36 wt. % |
| Ethyl chloride | 0.02 wt % |
| 1,1,2-Tetrachloroethane | 0.04 wt. % |
| Others | 0.06 wt % |

The reaction selectivity for EDC was about 99.61% based on ethylene.

The above procedure was repeated except that hexachloro-1,3-butadiene was not added at all. About 50 hours after initiation of the reaction, the liquid within the reactor was sampled and analyzed by gas chromatography. Hexachloro-1,3-butadiene was not detected. The product EDC was also sampled and analyzed by gas chromatography. The by-products in the product were as follows:

| | |
|---|---|
| 1,1,2-Trichloroethane | 0.93 wt. % |
| Ethyl chloride | 0.02 wt. % |
| 1,1,2-Tetrachloroethane | 0.11 wt. % |
| Others | 0.10 wt. % |

The reaction selectivity for EDC under the above conditions was about 99.11% based on ethylene.

EXAMPLE 8

The reaction was carried out in the same manner as in Example 7 except that tetrachloroethylene (concentration of tetrachloroethylene dissolved: 300 wt. ppm) was used instead of hexachloro-1,3-butadiene, the reactor top pressure was about 2.7 kg/cm$^3$G and the reaction temperature was about 130° C.

About 50 hours after initiation of the reaction, the product EDC was sampled and analyzed. The by-products in the product EDC were as follows:

| | |
|---|---|
| 1,1,2-Tetrachloroethane | 0.25 wt. % |
| Ethyl chloride | 0.02 wt. % |
| 1,1,2-Tetrachloroethane | 0.02 wt. % |
| Others | 0.03 wt. % |

The reaction selectivity for EDC was about 99.74% based on ethylene.

The above procedure was repeated except that tetrachloroethylene was not added at all.

About 50 hours after initiation of the reaction, the product EDC was sampled and analyzed. The by-products in the product EDC were as follows:

| | |
|---|---|
| 1,1,2-Trichloroethane | 0.87 wt. % |
| Ethylene chloride | 0.02 wt. % |
| 1,1,2-Tetrachloroethane | 0.09 wt. % |
| Others | 0.11 wt. % |

The reaction selectivity for EDC was about 99.16% based on ethylene.

EXAMPLE 9

The reaction was conducted in the same manner as in Example 7 except that hexachloro-1,3-butadiene was added so that the concentration of hexachloro-1,3-butadiene dissolved was 60 wt. ppm, the column top pressure was set at 1.8 kg/cm$^3$G and the temperature was held at 120° C.

About 50 hours after initiation of the reaction, the product EDC was sampled and analyzed. The by-products in the product EDC were as follows:

| | |
|---|---|
| 1,1,2-Trichloroethane | 0.19 wt. % |
| Ethyl chloride | 0.02 wt. % |
| 1,1,2-Tetrachloroethane | 0.02 wt. % |
| Others | 0.03 wt. % |

The reaction selectivity for EDC was about 99.79% based on ethylene.

The above procedure was repeated except that hexachloro-1,3-butadiene was not added at all.

About 50 hours after initiation of the reaction, the product EDC was sampled and analyzed. The by-products in the product EDC were as follows:

| | |
|---|---|
| 1,1,2-Trichloroethane | 0.68 wt. % |
| Ethyl chloride | 0.02 wt. % |
| 1,1,2-Tetrachloroethane | 0.08 wt. % |
| Others | 0.10 wt. % |

The reaction selectivity for EDC was about 99.31% based on ethylene.

EXAMPLE 10

A stainless steel reactor A equipped with a circulation path, shown in FIG. 6, was charged with liquid EDC, and anhydrous ferric chloride was added at a concentration of 600 wt. ppm as dissolved. From near the bottom of the reactor, ethylene 1 and chlorine 2 were respectively fed at a rate of 50 Nm³/hr. The feed chlorine contained about 1.0 mole % of oxygen. The reaction temperature was maintained at 135° C. and the reaction medium vapor generated by the heat of reaction was led into a gas-liquid contact section D connected to the top of the reactor A and brought into continuous counter-flow contact with the condensate of the column top vapor introduced through conduit 3. The heat of reaction was recovered by a heat exchanger (condensor) B disposed on and connected with the top of the gas-liquid contact section D through conduit 5. The condensate was led to a tank C, and the uncondensed gases were discharged from the tank C. The EDC produced by the reaction was continuously withdrawn from near the intermediate position of the gas-liquid contact section D through conduit 4. The liquid reaction mixture was not withdrawn.

After about 10 days of continuous operation, the composition of impurities included in the liquid in the reactor and those included in the product EDC became constant. The reaction mixture was sampled and analyzed by gas chromatography, whereby it was detected that about 250 wt. ppm of hexachloro-1,3-butadiene was dissolved. The product EDC contained the following by-products.

| | |
|---|---|
| 1,1,2-Trichoroethane | 0.39 wt. % |
| Ethyl chloride | 0.02 wt. % |
| 1,1,2,2-Terachloroethane | 0.05 wt. % |
| Hexachloro-1,3-butadiene | 0.0002 wt. % |
| Others | 0.05 wt. % |

The reaction selectivity for EDC was about 99.60% based on ethylene.

The above procedure was repeated except that, in order to obtain high-purity EDC by distillation of the product EDC, the reaction mixture was continuously withdrawn.

The rate of withdrawal of the liquid reaction mixture was about 10% based on the amount of the product EDC, that was about 20 kg/hr.

The amount of EDC obtained by distillation for purification was about 200 kg/hr. Since the reaction mixture withdrawn entrained some of dissolved ferric chloride, the corresponding amount of anhydrous ferric cloride was added so as to maintain its concentration.

After 10 days of continuous operation, the liquid withdrawn from the reactor was sampled and analyzed for by-products. The results are as follows:

| | |
|---|---|
| 1,1,2-Trichloroethane | 8.25 wt. % |
| Ethyl chloride | 0.005 wt. % |
| 1,1,2,2-Tetrachloroethane | 2.31 wt. % |
| Hexachloro-1,3-butadiene | 0.002 wt. % |
| Others | 1.56 wt. % |

The concentrations of impurities in the product EDC obtained after purification by distillation were as follows:

| | |
|---|---|
| 1,1,2-Trichloroethane | 0.01 wt. % |
| Ethyl chloride | 0.02 wt. % |
| 1,1,2,2-Tetrachloroethane | 0.001 wt. % |
| Hexachloro-1,3-butadiene | not detected |
| Others | 0.04 wt. % |

The reaction selectivity for EDC calculated from the total amount of these by-products was about 99.0% on the ethylene basis.

What we claim is:

1. A method of producing dichloroethane which comprises feeding ethylene and chlorine into a liquid reaction medium containing dichloroethane as a main component in a reactor which comprises a reaction zone and a gas-liquid contact device at the top part of the reactor above said reaction zone, reacting the ethylene and chlorine in the reaction zone of the reactor at a temperature which is not lower than the boiling point of dichloroethane at atmospheric pressure, to produce dichloroethane and to generate a vapor of the reaction medium, leading the reaction medium vapor through said gas-liquid contact device at the top of the reactor to a heat giving side of an exchanger whose heat receiving side is utilized as a reboiler for a distillation column, thereby condensing the reaction medium vapor and recovering the latent heat resulting from condensation of the vapor in the heat exchanger, returning the resulting condensate of the reaction medium vapor from the heat exchanger to said gas-liquid contact device of the reactor, thereby said condensate is brought into contact with the reaction medium vapor, removing as a product a part of the condensate subsequently to its contact with the reaction medium vapor, while conducting the remainder of the condensate subsequently to its contact with the reaction medium vapor to the reaction zone of the reactor, and purifying in said distillation column at least one member selected from the group consisting of dichloroethane produced by the reaction of ethylene and chlorine, dichloroethane produced in a separate process of oxychlorination of ethylene, and uncracked dichloroethane recovered in a separate process of thermally cracking dichloroethane.

2. The method of claim 1, wherein said part of the condensate of the reaction medium vapor which is taken out of the reactor is introduced into a low boiling distillation column from the top of which is discharged a low-boiling fraction gas which is then introduced into the upper part of said gas-liquid contact device of the reactor.

3. The method of claim 1, wherein the liquid reaction medium contains at last 0.003% by weight of a chlorinated aliphatic unsaturated hydrocarbon of the formula:

wherein n is an integer of 1 to 3.

4. The method of claim 3, wherein the chlorinated aliphatic unsaturated hydrocarbon is tetrachloroethylene, hexachloro-1,3-butadiene or a mixture thereof.

* * * * *